United States Patent [19]

Cioca

[11] 4,412,947
[45] Nov. 1, 1983

[54] COLLAGEN SPONGE

[75] Inventor: Gheorghe Cioca, Coatesville, Pa.

[73] Assignee: Seton Company, Newark, N.J.

[21] Appl. No.: 382,133

[22] Filed: May 26, 1982

Related U.S. Application Data

[63] Continuation-in-part of Ser. No. 184,536, Sep. 5, 1980, abandoned, and Ser. No. 190,372, Sep. 24, 1980, Pat. No. 4,374,121, which is a continuation-in-part of Ser. No. 74,738, Sep. 12, 1979, Pat. No. 4,279,812.

[51] Int. Cl.$^3$ .......................... C07G 7/00; C08H 1/06; C08L 89/04; C08L 89/06
[52] U.S. Cl. ................. 260/123.7; 106/124; 106/155; 604/368; 128/DIG. 8; 424/116; 424/177
[58] Field of Search ..................... 260/123.7; 106/155, 106/124

[56] References Cited

U.S. PATENT DOCUMENTS

| | | | |
|---|---|---|---|
| 2,934,447 | 4/1960 | Highberger et al. | 260/123.7 X |
| 3,157,524 | 11/1964 | Artandi | 260/123.7 X |
| 3,178,301 | 4/1965 | Veis et al. | 260/123.7 X |
| 3,514,518 | 5/1970 | Charier-Vadrot | 260/117 X |
| 3,628,974 | 12/1971 | Battista | 260/123.7 X |
| 3,632,361 | 1/1972 | Battista | 260/123.7 X |
| 3,742,955 | 7/1973 | Battista et al. | 106/161 X |
| 3,939,831 | 2/1976 | Cioca et al. | 128/156 |
| 4,193,813 | 3/1980 | Chvapil | 260/123.7 X |
| 4,279,812 | 7/1981 | Cioca | 260/123.7 |
| 4,295,894 | 10/1981 | Cioca et al. | 260/123.7 X |
| 4,374,121 | 2/1983 | Cioca | 260/123.7 X |

Primary Examiner—Howard E. Schain
Attorney, Agent, or Firm—Webb, Burden, Robinson & Webb

[57] ABSTRACT

A process for preparing a coherent porous collagen sheet material is comprised of forming natural insoluble particulate collagen in substantially pure form and suspending the particulate collagen in a weak aqueous organic acid solution while maintaining the collagen in particulate form. The suspension is freeze-dried to form a coherent porous native collagen sheet material which is useful as a wound dressing, burn dressing, hemostatic sheet or the like.

9 Claims, No Drawings

COLLAGEN SPONGE

CROSS-REFERENCE TO RELATED APPLICATIONS

This application is a continuation-in-part of co-pending U.S. Application Ser. No. 184,536, filed Sept. 5, 1980 now abandoned; and a continuation-in-part of U.S. Application Ser. No. 190,372, filed Sept. 24, 1980, now U.S. Pat. No. 4,374,121, which is a continuation-in-part of U.S. Application Ser. No. 74,738, filed Sept. 12, 1979, now U.S. Pat. No. 4,279,812, issued July 21, 1981.

BACKGROUND OF THE INVENTION

1. Field of the Invention

This invention relates to collagen, and more particularly, to a collagen sponge formed of natural insoluble collagen.

2. Description of the Prior Art

"Natural insoluble collagen" as used herein means and refers to collagen which cannot be dissolved in an aqueous alkaline or in any inorganic salt solution without chemical modification, and includes hides, splits and other mammalian or reptilian coverings. More particularly, "natural insoluble collagen" means and refers to the corium which is the intermediate layer of a bovine hide between the grain and the flesh sides.

In young animals there is little intermolecular and interfibrillar crosslinking which provides for some degree of solubility of the collagen. However, during the aging process both intermolecular and interfibrillar crosslinking occurs, thus making the collagen insoluble.

The use of collagen in substantially pure form has been proposed for many uses, including for burn dressings as disclosed in U.S. Pat. Nos. 3,939,831 and 3,514,518, and similar medical applications as disclosed in U.S. Pat. Nos. 3,157,524 and 3,628,974.

U.S. Pat. No. 3,637,642 is exemplary of a process for dissolving insoluble collagen and regenerating the fiber.

Further methods have been proposed for solubilizing and reconstituting collagen with the use of enzymes to sever intra and interfibrillar bonds, such as is disclosed in U.S. Pat. No. 3,034,852, and other processes have been proposed for converting collagen fibrous masses to sheet-like material, such as in U.S. Pat. Nos. 2,934,447 and 2,934,446.

Further, according to U.S. Pat. Nos. 3,939,831 and 3,742,955, medicinal dressings can be prepared from collagen having dispersed therein antibiotics and the like to aid in the healing of skin which has been burned.

Also, according to U.S. Pat. No. 3,742,955, fibrous collagen has been proposed which has hemostatic and wound binding properties. The collagen is in the form of a fluffy fibrous product which may be converted into nonwoven webs or mats by mechanical techniques.

In accordance with the present invention, a collagen sponge is provided which derives its integrity through chemical bonding of the particulate native collagen. Further, the collagen sponge in accordance with the present invention has wound healing properties and hemostatic properties.

BRIEF DESCRIPTION OF THE INVENTION

A process for preparing a coherent porous collagen sheet material is comprised of forming natural insoluble particulate collagen in substantially pure form and suspending the particulate collagen in a weak aqueous organic acid solution while maintaining the collagen in particulate form. The suspension is freeze-dried to form a coherent porous native collagen sheet material which is useful as a wound dressing, burn dressing, hemostatic sheet or the like.

DETAILED DESCRIPTION OF THE INVENTION

The natural insoluble particulate collagen in accordance with the invention is preferably derived from a bovine hide which has been dehaired by liming, degreased to produce substantially pure native insoluble collagen fibers, and granulated to a particle size of less than 1 millimeter, and preferably less than 0.5 millimeter. The degreasing and granulation can be accomplished with materials, apparatus and methods known to those skilled in the art. It is important that the final particulate native collagen used to prepare the sponge in accordance with the invention retain its crosslinkages, i.e. insolubility in water, aqueous acid, aqueous base or salt, but yet remain substantially pure so as to maintain the nonantigenic and nonallergenic characteristics recognized in the native collagen.

After forming the particulate native collagen in substantially pure form, the particulate collagen is dispersed in a weak aqueous organic acid solution. The aqueous organic acid solution contains up to about 5 percent by weight of the collagen, and preferably up to 3 percent by weight of the collagen in particulate form. The acids useful for forming the aqueous acid solution are the weak organic acids, such as acetic, citric, lactic, ascorbic, tartaric and the like. Preferably, the pH of the aqueous acid solution is adjusted to below 4 in order to obtain good particulate collagen dispersion and, in the case of ascorbic acid, a 1 percent solution is sufficient; whereas acetic or tartaric acid requires a 0.5 percent acid solution. Preferably, the pH of the aqueous solution should be about 3 to 4.

After forming the solution, the solution is frozen with a temperature reduction rate of about $-18°$ to $-24°$ C./hour so that the ice crystals formed are extremely small and do not sever the crosslinkages or collagen chains, thus retaining the nativity and natural insoluble characteristics of the particulate collagen. To obtain the desired rate of freezing, the collagen dispersion is placed in a freezer at $-60°$ to $-70°$ C.

The frozen dispersion, at an initial temperature of $-60°$ to $-70°$ C., is then placed in a freeze-dryer and vacuum sublimated at $10^{-3}$ to $10^{-5}$ torr. The freeze-drying process requires about 12 to 24 hours with a final temperature of about 30° C.

Although there is a prevention of the destruction of the chemical bonds in the collagen by freezing, there is a minor amount of cryogenic destruction. This cryogenic destruction provides locations on the collagen product for reactive and associative sites which, throughout the freeze-drying process, provides reactivity and thus binds the individual collagen fibers to each other to form the coherent sheet in accordance with the invention.

Thus, although reactive sites are formed, the collagen retains its native characteristics typically maintaining the triple helical configuration of the fibrils, with the fibrils retaining their alignment with an axial periodicity of about 640 angstroms.

Thus, the collagen sponge prepared in accordance with the invention derives its integrity from the specific freeze-drying process while maintaining its nativity.

Typically, the collagen sponge prepared in accordance with the invention has a bulk density of 0.005 to 0.0065 gr/cm$^3$ and is at a preferred thickness of 5 to 7 millimeters.

It must be understood that the purity and nativity of the particulate collagen used to form the dispersion must be maintained throughout the process.

The collagen sponge prepared in accordance with the present invention has substantial advantages when used for medical applications.

The collagen sponge in accordance with the invention dessicates the wound and coagulates secretions while maintaining its capillary and hydrophilic action, even after plasma and secretion incorporation. Thus, the collagen sponge behaves as a dry, nonretentive eschar allowing for quick drainage, thus providing drying of the wound through its coagulant power, yet easily removable from the wound without pain to the patient. It has been found that the collagen sponge in accordance with the invention does not adhere to the wound lining tissue, nor is the tissue negatively influenced by the collagen sponge.

Additionally, the collagen sponge is compatible with most medications, such as antibiotics and the like, so long as the pores are not clogged, and is in fact usable in combination with other dressings. Additionally, the sponge provides protection to the wound against mechanical trauma.

Because of the high degree of purity of the native collagen used to prepare the sponge and the purity of the resultant native collagen sponge, the sponge is non-allergenic and nonantigenic. Further, the collagen sponge in accordance with the invention provides a number of physical advantages since it is easily stored and handled by treating personnel while also being easily supported by the patient without the discomfort normally associated with large gauze dressings.

The process and product of the invention will be more fully described with reference to the following examples.

EXAMPLE I

Two hundred pounds of lime split bovine fresh hide were processed in a wooden drum containing 600 pounds of water at 20° C. and 6 pounds of 37 percent hydrochloric acid. After charging the splits, the water and the acid, the drum was rotated for 4 hours. This initial process was conducted in order to remove residual lime from the collagen. After deliming, the splits were washed with water for 3 hours in the wooden drum at a float of 300 percent, and the water was changed after each hour. The washed splits were then treated with a degreasing agent, and in this example, of 3 percent solution of a nonionic surfactant sold under the trade name Triton X-114. The washing of the splits was done at a float of 200 percent for 5 hours at room temperature in a wooden drum. The degreased splits were washed with water for 4 hours at room temperature at a float of 300 percent, changing water after each hour. The splits were dried by toggling in extended form so that excess grease was removed. The toggling was conducted for 16 hours at 140° F. After drying, the collagen was in relatively pure form and was immersed in an organic solvent, and in this example, petroleum ether at a float of 300 percent for 2 hours. The splits were dried and cut into square pieces of 15×15 inches. The pieces were pulverized to a particle size of 0.032 to 0.4 millimeter and the powder was extracted with petroleum ether and again dried to remove any residual oils, fats or like soluble hide constituents. The dry particulate native collagen had the following chemical analysis:

% Protein—90.7
% Salt Concentration (as NaCl)—0.2
Acidity, milliequivalents/gr.—68.7
% Hydroxyproline—10.36
pH (1% aqueous dispersion)—3.5

The physicochemical characteristics of the particulate collagen were as follows:

$\beta/\alpha$ chain ratio of collagen—34/66
Molecular weight (avg.)—140,000
Temperature range to denaturation—31.7° to 59.2° C.

EXAMPLE II

The natural insoluble collagen in particulate form prepared in accordance with Example I was dispersed in a 0.5 percent by weight aqueous solution of acetic acid. The dispersion was 3 percent by weight of the particulate collagen of Example I. The pH of the particulate collagen dispersion was about 3.5.

The collagen dispersion was charged to a tray having a thickness of 10 millimeters and dimensions of 20 centimeters by 20 centimeters.

The collagen dispersion on the tray was placed in a freezer at about −65° C. and frozen at a temperature reduction rate of −18° to −24° C./hour until it had a final temperature of −60° to −70° C. The frozen solution on the tray was placed in a freeze-dryer and a vacuum was applied thereto of $10^{-3}$ to $10^{-5}$ torr for 16 hours. The collagen solution had an initial temperature of −65° C. and a final temperature of 30° C. after the 16 hour vacuum sublimation process.

Thus, upon reaching the final temperature of 30° C., the collagen sponge was a coherent open-celled sheet having hemostatic properties as well as being capable of transporting wound secretion through the sponge thickness while maintaining its capillary and hydrophilic action. The collagen sponge in accordance with Example II had a bulk density of 0.005 gr/cm$^3$ and a thickness of 5 millimeters.

Although the invention has been described with reference to particular processes and particular materials, the invention is only to be limited so far as is set forth in the accompanying claims.

I claim:

1. A process of preparing a coherent, porous collagen sheet material comprising:
   forming natural insoluble particulate collagen in substantially pure form;
   suspending said particulate collagen in a weak aqueous organic acid solution while maintaining said collagen in particulate form; and
   freeze-drying said suspension to form a coherent, porous native collagen sheet material.

2. The process of claim 1 wherein said natural insoluble particulate collagen has a particle size of less than about 1 millimeter.

3. The process of claim 2 wherein said natural insoluble particulate collagen has a particle size of less than about 0.5 millimeter.

4. The process of claim 1 wherein said weak organic acid is selected from the group consisting of acetic acid, citric acid, lactic acid, ascorbic acid and tartaric acid.

5. The process of claim 1 wherein said particulate collagen suspension is at a level of up to about 5 percent by weight collagen.

6. The process of claim 5 wherein said particulate collagen suspension is at a level of up to about 3 percent by weight collagen.

7. The process of claim 1 wherein said aqueous acid solution is at a level of up to 1 percent by weight acid.

8. The process of claim 1 wherein said freeze-drying is conducted by freezing said solution to effect a temperature reduction rate of $-18°$ to $-24°$ C./hr., and vacuum drying said solution at $10^{-3}$ to $10^{-5}$ torr for at least 12 hours.

9. A coherent, porous native collagen sheet material produced in accordance with the process of claim 1.

* * * * *